United States Patent [19]

Parker

[11] 3,941,762

[45] Mar. 2, 1976

[54] O-ACYL DERIVATIVES OF ANTIBIOTIC EM-49
[75] Inventor: William Lawrence Parker, Pennington, N.J.
[73] Assignee: E. R. Squibb & Sons, Inc., Princeton, N.J.
[22] Filed: July 8, 1974
[21] Appl. No.: 486,557

Related U.S. Application Data
[63] Continuation-in-part of Ser. No. 357,735, May 7, 1973, abandoned.

[52] U.S. Cl.............. 260/112.5 R; 195/29; 424/177
[51] Int. Cl.² C07C 103/52; C08H 1/00; C12B 1/00
[58] Field of Search.................. 424/115; 260/112.5; 195/29

[56] References Cited
UNITED STATES PATENTS
3,753,970   8/1973   Bouchaudon et al........ 260/112.5 R
3,817,973   6/1974   Bouchaudon et al........ 260/112.5 R

OTHER PUBLICATIONS

Miller, The Pfizer Handbook of Microbial Metabolites, McGraw–Hill Book Co., Inc., N.Y., N.Y., 1961, p. 371.

*Primary Examiner*—Lewis Gotts
*Assistant Examiner*—Reginald J. Suyat
*Attorney, Agent, or Firm*—Lawrence S. Levinson; Merle J. Smith

[57] ABSTRACT

Antibiotic EM-49, an antimicrobially active material obtained from the microorganism *Bacillus circulans* ATCC 21656, is chemically treated to acylate the hydroxyl group, thereby obtaining O-acyl derivatives which are effective against a variety of bacteria and fungi.

33 Claims, 12 Drawing Figures

O-ACYL DERIVATIVES OF ANTIBIOTIC EM-49

This application is a continuation-in-part of application Ser. No. 357,735, filed May 7, 1973, now abandoned.

SUMMARY OF THE INVENTION

Antibiotic EM-49, obtained from the microorganism *Bacillus circulans* ATCC 21656, is an antimicrobially active material which has been described in the copending application of Murao, Meyers and Parker, Ser. No. 242,047, filed Apr. 7, 1972, U.S. Pat. No. 3,856,938, issued Dec. 24, 1974. This antibiotic may be separated into component parts comprising closely related octapeptide antibiotics as described in that application.

It has now been found that the antibiotic EM-49, described in the foregoing application, has one hydroxyl group which may be acylated, e.g., by treatment with an acid anhydride or acid chloride (with protection of the free amino groups) to obtain the O-acyl derivative of antibiotic EM-49.

This invention therefore relates to O-acyl derivatives of antibiotic EM-49 and certain intermediates therefor.

FIG. 3 shows the infrared spectrum of the O-acetyl derivative of antibiotic EM-49, tetrahydrochloride, in KBr.

DETAILED DESCRIPTION OF THE INVENTION

Figure 1:
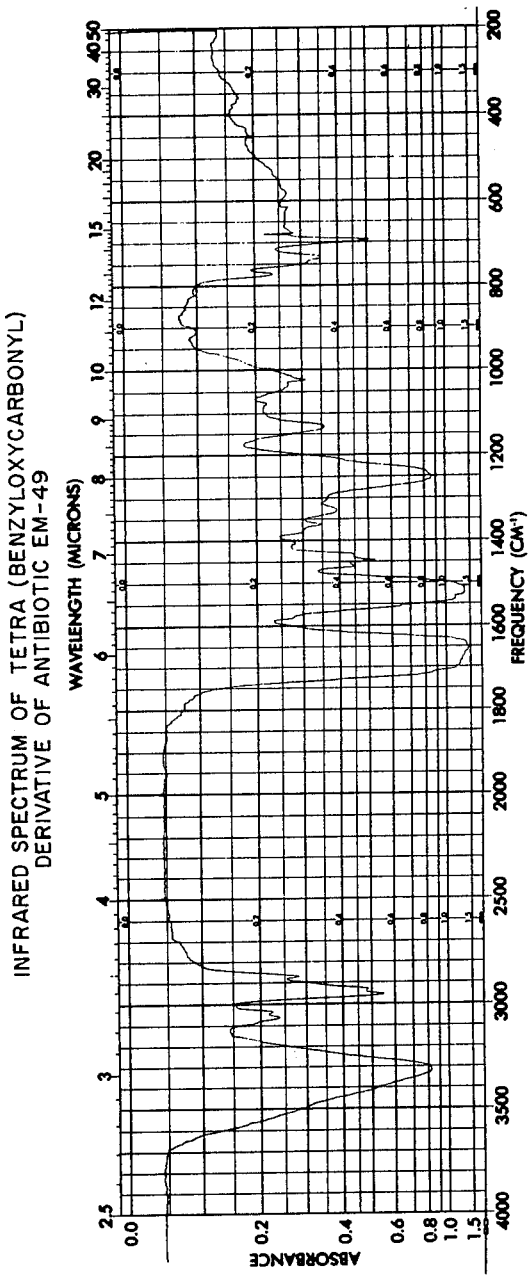
FIG. 1 shows the infrared spectrum of the tetra(benzyloxycarbonyl) derivative of antibiotic EM-49 in KBr.

Antibiotic EM-49 is a new antibiotic produced by the cultivation under controlled conditions of the microorganism *Bacillus circulans* ATCC 21656 as described in the copending application of Murao et al. referred to above. Briefly, the production of antibiotic EM-49 involves cultivating the microorganism *Bacillus circulans* ATCC 21656 in an aqueous nutrient medium comprising an assimilable carbohydrate and an assimilable nitrogen source under submerged aerobic conditions until substantial antibiotic activity is imparted to the medium.

The fermentation broth is acidified, the solids are separated by filtration, washed with water and the water washings are added to the filtrate. The combined washings and filtrate are extracted with a water immiscible alcohol, e.g., an aqueous alkanol solvent like a lower alkanol, preferably n-butanol. The alcoholic solution is concentrated and the antibiotic is precipitated with an organic solvent, e.g., ethyl acetate, acetonitrile, ether or preferably with acetone. The product may be further purified by counter-current distribution in a water-alcohol-organic acid system, e.g., n-propanol-n-butanol-water-acetic acid, or by formulation of the helianthate salt and regeneration of the antibiotic from this salt.

These procedures result in the isolation of the product, antibiotic EM-49, as the acid salt corresponding to the acid used for acidification of the broth or regeneration from the helianthate. The salt can be converted to the free base by neutralization with a base like ammonium hydroxide, sodium hydroxide, barium hydroxide, or the like, and extraction with a water immiscible alcohol like n-butanol.

The antibiotic EM-49, obtained in this manner is an antimicrobially active substance which can be separated by ion exchange chromatography into four major fractions containing active materials closely related structurally. These closely related octapeptide antibiotics, each having four free amino groups and a hydroxyl group, are referred to herein collectively as antibiotic EM-49 and, unless specifically indicated otherwise, the term is intended to refer to the antibiotic and its individual components.

Antibiotic EM-49 and its components are active against various microorganisms like fungi, bacteria and yeasts as *Staphylococcus aureus*, *Trichomonas vaginalis*, *Streptococcus pyogenes*, *Escherichia coli*, *Pseudomonas aeruginosa*, *Candida albicans* and *Trichophyton mentagrophytes*.

Antibiotic EM-49 has been tentatively assigned the following structure:

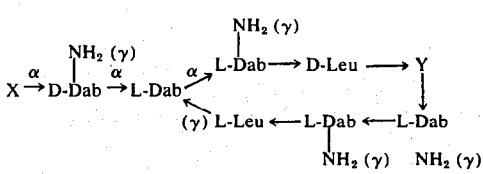

"Dab" represents 2,4-diaminobutyric acid and the other symbols have the conventional meanings in peptide chemistry, i.e., "Leu" is leucine and the arrows and Greek symbols indicate the attachment.

Y represents L-leucine (L-Leu) or L-phenylalanine (L-Phe).

X represents the C$_{10}$ or C$_{11}$ acyl group (referred to below) having the structure:

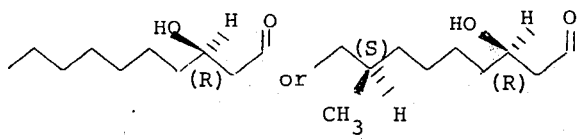

The β-hydroxy-n-decanoic acid (corresponding to the acyl group shown above) is a relatively minor constituent (ca, 10%) of the mixture of fatty acids produced by acid hydrolysis of antibiotic EM-49.

This antibiotic has one β-hydroxy fatty acid residue per molecule. The fatty acid residue has been identified as a $C_{10}$- or $C_{11}$-β-hydroxy fatty acid. This hydroxyl group can be acylated in the intact antibiotic molecule by treatment with an acylating agent, e.g., an acid anhydride such as acetic anhydride, or an acyl halide, preferably the acyl chloride, such as acetyl chloride, butyryl chloride, hexanoyl chloride, octanoyl chloride or the like. As used herein the actyl derivatives and acyl halides refer to those acyl radicals, i.e., lower alkanoyl radicals, having two to eight carbons in the acid moiety, including acetyl, propionyl, butyryl, pentanoyl, hexanoyl, heptanoyl and octanoyl as well as their branched chain isomers. The straight chain members are preferred, especially acetyl, butyryl, hexanoyl and octanoyl. Especially preferred groups are the acyl derivatives with four to eight carbons in the acyl group, particularly butyryl, hexanoyl and octanoyl and their acid addition salts. The hexanoyl derivative and acid addition salts thereof is a particular choice.

The acylation is effected by treating antibiotic EM-49, its salt or protected derivative thereof with the acylating agent in an inert organic solvent, e.g., a dialkyl ketone like methyl ethyl ketone, or an acid like trifluoroacetic acid, at a temperature within the range of about −5° to 120° centigrade.

Because of the presence of the free amino groups it is desirable to protect these free amino groups prior to the acylation of the hydroxy group. The protection is effected in any conventional manner by introducing the carbobenzoxy group, t-butoxycarbonyl group, or the like, or by protonation in a strongly acidic medium, e.g., trifluoroacetic acid.

The O-acyl derivatives of antibiotic EM-49 are acylated at the hydroxyl group of the β-hydroxy fatty acid residue (represented by X), and the acylated fatty acid moiety represented by X' has the structure:

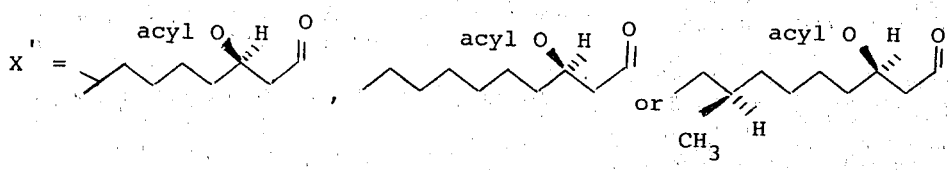

wherein $R^1$ is $C_7H_{15}$ or $C_8H_{17}$ and $R^2$ is a lower alkanoyl group, i.e., the acyl group of a lower fatty acid having two to eight carbons.

Two preferred alternative procedures are as follows:

Antibiotic EM-49 or an acid salt like the hydrochloride, hydrobromide, acetate, etc., is treated to introduce the carbobenzoxy group to protect the free amino groups. This is effected by reacting the starting material with a carbobenzoxy halide like carbobenzoxy chloride in a ratio of about four moles of carbobenzoxy chloride per mole of EM-49 in an inert organic solvent, preferably methyl ethyl ketone, in the presence of water and an acid binding agent like sodium bicarbonate. This is done at about ambient temperature and the reaction is complete in a period of about one hour or less. The protected product is then preferably separated from the reaction mixture, e.g., by extraction with an organic solvent like ethyl acetate, chloroform, methylene chloride or the like, the first being preferred. The product is then isolated, e.g., by removal of the solvent under reduced pressure or by precipitation with hexane.

This tetra(benzyloxycarbonyl) derivative of antibiotic EM-49 is then treated to acylate to aforementioned hydroxyl group by reaction with an acid anhydride like acetic anhydride using a catalyst like sodium acetate. An inert organic solvent like dioxane or tetrahydrofuran may be used or the acetic anhydride itself may serve as the medium. About one to five moles of acid anhydride, per mole of antibiotic is used, but this is increased by fifteen to sixty times if the anhydride also serves as the reaction medium. A temperature within the range of about 70° to 120° celsius is employed. Usually about one half hour to five hours are sufficient for completion of the acylation reaction. Cooling to room temperature and addition of water to destroy the acylating agent then permits isolation of the acylated product. This is effected by extraction with an inert organic solvent such as ethyl acetate, which is preferred, chloroform, methylene chloride or the like, then evaporating the solvent.

The protecting groups are then removed by conventional procedures such as by treatment with hydrogen in the presence of palladium-carbon catalyst or with hydrogen bromide in acetic acid.

For example, when the acyl group is n-hexanoyl, X' is structurally depicted as follows:

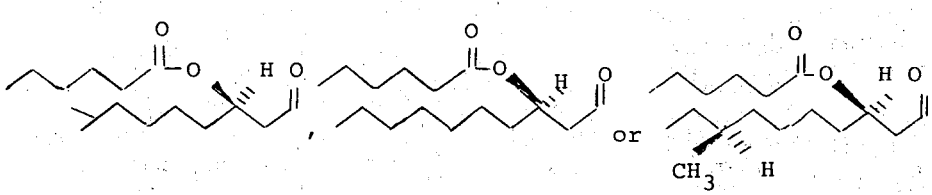

For convenience hereinafter X' will be depicted as follows:

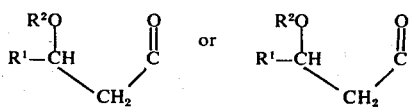

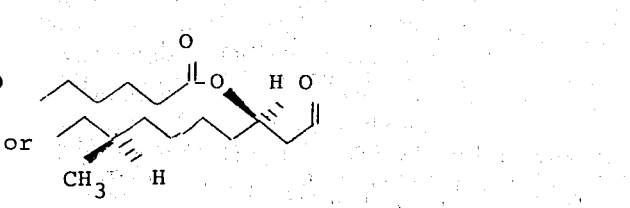

The O-acyl derivative of antibiotic EM-49 is then obtained upon separation from the reaction mixture, e.g., by precipitation with an organic solvent miscible with the reaction solvents, for example, ether, ethyl acetate, chloroform or the like.

It is preferable at this point to convert the product to the hydrochloride which is a form convenient for characterization, analysis and various testing procedures. This is done by conventional procedures such as ion exchange with a strong base exchanger in the chloride form or by conversion to the free base with sodium hydroxide or the like and acidification with hydrochloric acid.

An alternative procedure is the treatment of a solution of the antibiotic EM-49 or its salt in a strongly acidic medium with the acyl halide or acid anhydride, e.g., an acyl chloride like acetyl chloride, which is preferred, acetyl bromide, hexanoyl chloride, octanoyl chloride or acetic anhydride. Strongly acidic media like trifluoroacetic acid, which is preferred, acetic acid containing anhydrous HCl, or nitromethane containing anhydrous HBr can be used. The acylation reaction occurs at a temperature of about −5° to 25° centigrade within about one half to two hours. Higher temperatures may be required when an acid anhydride is used as the acylating agent. About one to fifteen moles of acylating agent per mole of antibiotic is used in the reaction. The product is then worked up in the same manner as described above (after removal of the protecting groups).

By dissolving this product in water and passing the solution through an ion exchange resin having the desired salt anion, or by treating the free base with the inorganic or organic acid having the desired anion, other inorganic or organic acid addition salts such as the nitrate, hydrobromide, hydroiodide, sulfate, acetate, tartrate, borate, succinate, etc. are obtained. One or more molecular proportions of the acid can be present in the acid salt. Illustrative salts are shown in the examples and other acid salts are similarly produced.

The O-acyl derivatives of antibiotic EM-49 and their salts are active against yeasts, fungi, protozoa and gram-positive and gram-negative bacteria, e.g., *Staphylococcus aureus, Staphylococcus epidermis, Streptococcus pyogenes, Corynebacterium minutissimum, Escherichia coli, Pseudomonas aeruginosa, Candida albicans, Trichophyton mentagrophytes* and *Trichomonas vaginalis*. The O-acyl derivatives of antibiotic EM-49 or physiologically acceptable salts thereof are therefore useful as antimicrobial agents either as environmental disinfectants or sterilizing mediums, e.g., in a spray, solution or dust containing up to about 1% of the substance in a conventional carrier, or to combat infections in various animal species due to microorganisms such as those enumerated, e.g., topically in a conventional cream or ointment containing up to about 1% of the substance. For example, a composition containing ½ to 1% of the active substance in a cream base protects against a topical *Staphylococcus aureus* infection in mice.

The following examples are illustrative of the invention. Temperatures are on the celsius scale.

EXAMPLE 1

Antibiotic EM-49 is prepared as described in the copending application referred to above.

a. Yeast beef agar slants are seeded with *Bacillus circulans* ATCC 21656 (a culture of which is on deposit and available from the American Type Culture Collection, Rockville, Maryland). They are incubated overnight at 37°C. and then used to inoculate 50 ml. of an aqueous soybean meal medium contained in 250 ml. Erlenmeyer flasks. The composition of the germination medium is:

| Medium | Grams |
| --- | --- |
| Soybean meal | 15.0 |
| Dehydrated mashed potato | 15.0 |
| Glucose | 50.0 |
| $CoCl_2 \cdot 2H_2O$ | 0.005 |
| $CaCO_3$ | 10.0 |
| Distilled water to | 1 liter |

This medium is sterilized for 30 minutes at 121°C and at 15 lbs. steam pressure prior to use. The inoculated germination flasks are incubated at 25°C. for 72 hours on a rotary shaker, operating at 280 r.p.m. with a 2 inch throw.

A 2.5% (v/v) transfer is made from the germination flask to 500 ml. Erlenmeyer flasks containing 100 ml. of an aqueous corn steep liquor medium. The composition of this medium is:

| Medium | Grams |
| --- | --- |
| Corn steep liquor | 6.0 |
| $(NH_4)H_2PO_4$ | 3.0 |
| Yeast extract | 2.5 |
| Dextrose | 10.0 |
| Distilled water to | 1 liter |
| Adjust pH to 7.0 | |

The fermentation flasks are incubated and agitated as are the germination flasks. Samples are taken at 3 to 6 days, and examined by paper chromatography and bioassay. For paper chomatography suitable amounts of a butanol extract of the acidified beer are spotted on sheets of Whatman No. 1 paper and the chromatograms developed with a solvent of the following composition: n-butanol, acetic acid, water (4:1:5, by volume). The upper phase of this solvent system is utilized as the solvent. In this system, EM-49 (as the hydrochloride) has an $R_f$ value of 0.71. The antibiotic is detected by bioautography against *Staphylococcus aureus* FDA 209P and *Escherichia coli* ATCC 10536. For bioassay, both organisms are used in conventional tube dilution assays.

b. A 250 liter batch of *Bacillus circulans* ATCC 21656 is fermented in a 100 gal. stainless steel vessel with the medium and operating conditions described below:

Stage 1

Inoculum: Culture of *Bacillus circulans* ATCC 21656 is preserved by storage in liquid nitrogen, and grown out when needed on yeast beef agar slants that have the following composition:

| Medium | Grams |
| --- | --- |
| Beef extract | 1.5 |
| Yeast extract | 3.0 |
| Peptone | 6.0 |
| Dextrose | 1.0 |
| Agar | 15.0 |
| Distilled water to 1,000 ml. | |

The medium is sterilized at 15 lbs. pressure and at 121°C. for 15 minutes prior to use.

Growth from the slant is used to inoculate the first germinator flasks.

| Medium | Grams |
| --- | --- |
| Soybean meal | 15.0 |
| Dehydrated mashed potato | 15.0 |
| Glucose | 50.0 |
| $CoCl_2 \cdot 2H_2O$ | 0.005 |
| $CaCO_3$ | 10.0 |
| Distilled water to 1000 ml. | |
| Sterilize at 121°C. for thirty minutes | |

100 ml. of this medium in a 500 ml. Erlenmeyer flask is incubated 72 hours on a rotary shaker at 25°C. The shaker operates at 280 r.p.m. with a 2 inch throw.

Stage 2

Inoculum: 100 ml. from first stage.
Medium: Same as the germinator medium of stage 1. The inoculum and 1,000 ml. of medium in a 4,000 ml. Erlenmeyer flask is incubated 72 hours at 25°C. on a rotary shaker. The shaker is operated at 280 r.p.m. with a 2 inch throw.

Stage 3

Inoculum: 3,000 ml. from stage 2.

| Medium | Grams |
| --- | --- |
| Corn steep liquor | 6.0 |
| $(NH_4)H_2PO_4$ | 3.0 |
| Yeast extract | 2.5 |
| Dextrose | 10.0 |
| Distilled water to 1,000 ml. | |
| Adjust to pH 7.0 | |
| $CaCO_3$ | 2.5 |

The inoculum is added to 250 liters of medium and incubated 144 hours. During incubation, the broth is aerated at the rate of 2.0 foot per minute superficial air velocity, at 10 p.s.i. During this period, the broth is agitated at the rate of 0.4 watt per liter and at 155 r.p.m.

c. The fermentation broth, obtained as described in part b (209 liters), is adjusted to pH 2.0 with 1.5 liters of concentrated hydrochloric acid. Filter aid (Hyflo, 15 kg.) is added to the acidified beer and the mixture filtered to give 41 kg. of insoluble material. The insoluble cake is washed with 10 liters of water and the washings combined with the filtrate to give 190 liters. The washed cake (41 kg.) is discarded.

d. The filtrate (190 liters) obtained in part c is extracted three times with 56 liter portions of water saturated n-butanol. The butanol layers (194 liters) are pooled and concentrated in vacuo, at a temperature less than 45° C., to a small volume (2.3 liters).

e. A 50 ml. portion of the concentrate obtained in part d is diluted with 750 ml. of acetone and the resulting precipitate is centrifuged. The precipitate is washed with acetone (60 ml.) by suspending it in the solvent and then centrifuging it. This is repeated using ethyl acetate (three 60 ml. portions) and finally ether (three 60 ml. portions). The precipitate is dried in air, powdered and dried in vacuo, giving 1.4 g. of a light-tan powder.

f. A 1.4 g. sample of the acetone-insoluble powder obtained in part e is further purified by counter-current distribution using a n-propanol-n-butanol-water-acetic acid (50:75:100:2 by volume) system. Twenty-nine transfers are made using 40 ml. of each phase per tube. The maximum activity, as determined by paper disc agar diffusion assay, is in tube 11. The contents of tubes 8–14 are combined and the solvents are removed in vacuo. The residue is dissolved in a little methanol and the antibiotic is precipitated by the addition of acetone and ether. The precipitate is washed well with ether, dried in air and then in vacuo, giving 0.466 g. of a light-tan powder. This material is primarily the basic peptide antibiotic EM-49, in the form of its hydrochloride salt.

g. The hydrochloride of antibiotic EM-49 is converted to the free base by counter-current distribution using a n-butanol-0.5 N $NH_4OH$ system. 1.01 g. of the hydrochloride of EM-49, prepared as in part f is processed in a 29 transfer counter-current distribution using 40 ml. each of upper and lower phases per tube. The contents of tubes 25–29 are combined, and the upper phase is separated and taken to dryness in vacuo. The residue is then dissolved in warm methanol (ca. 50 ml.). Ethyl acetate (50 ml.), benzene (50 ml.) and cyclohexane (50 ml.) are added. Removal of this solvent mixture in vacuo gives 0.75 g. of a nearly white powder that is the free base of the antibiotic EM-49. This material melts at 245°–248°C in an evacuated capillary. Analysis: C, 56.64; H, 8.65; N, 16.50; Cl, 0.0 h. One g. of the acetone-insoluble powder obtained as described in part e is dissolved as much as possible in 10 ml. of water. The insoluble material is removed by centrifugation, washed with 10 ml. of water and then the supernatants are combined.

One g. of methyl orange is suspended in 15 ml. of water. Five ml. of dimethylformamide is added and the mixture is warmed until the methyl orange just dissolves. This warm solution is added to the EM-49 solution. The mixture is cooled to room temperature and the solid is isolated by centrifugation, washed with 3 × 35 ml. of water and dried in vacuo.

The crude helianthate is dissolved as much as possible in 3 ml. of dimethylformamide and the insoluble material is removed by centrifugation, washing it with 2 × 3 ml. of dimethylformamide. The combined dimethylformamide solution is combined with 90 ml. of water, the precipitate is separated by centrifugation and this is washed with 3 × 30 ml. of water.

The helianthate of EM-49 is amorphous but is purified by reprecipitation from methanol-acetonitrile (2:1). This material is dried at 0.02 mm. and 100° for 18 hours and then allowed to equilibrate with atmospheric moisture. M.P. (Kofler hot stage): 242°–4°C. (dec.).

The EM-49 helianthate is converted to the hydrochloride by stirring with 10 ml. of 0.36 N hydrochloric acid for 20 minutes. The insoluble material is removed by centrifugation and washed with 2 × 5 ml. 0.36 N hydrochloric acid. The combined supernatant is then stirred with 320 mg. of Darco G-60 charcoal and filtered through diatomaceous earth, giving a nearly colorless solution.

The filtrate is extracted with two 10 ml. portions of n-butanol. Removal of the butanol in vacuo gives an amorphous solid. This is converted to a fine powder by dissolving the solid in a small quantity of methanol, adding ethyl acetate until the antibiotic precipitates, and then removing the solvent mixture in vacuo. The powder is then dried at 50° and 0.02 mm. for several (e.g., 5) hours and then equilibrated with atmospheric moisture overnight.

EXAMPLE 2 a. To a suspension of 329 mg. (1 meq.) of antibiotic EM-49 hydrochloride (obtained in Example 1 h) in 3.3 ml. of methyl ethyl ketone are added 6.6 ml. of water followed by 209 mg. (2.5 meq.) of sodium bicarbonate. This mixture is stirred and treated with 0.170 ml. (1 meg.) of carbobenzyloxy chloride (84% pure by nmr) at one time. The mixture is stirred at room temperature for 1 hour. Ethyl acetate is added and the organic phase is washed with water, 0.01 N hydrochloric acid and water again. The solution is taken to dryness in vacuo and the residue is precipitated from ehtyl acetate with hexane to obtain a fine white powder. This powder, the tetr(benzyloxycarbonyl) derivative of EM-49, , is dried in vacuo and then equilibrated with atmospheric moisture; water content = 2.29%, m.p. 159°–161°C.

Analysis: Found C. 59.87; H, 6.79; N, 11.11/ Adjusted to correspond to the anhydrous material: C, 61.27; H, 6.69; N, 11.37. Calc'd. for $C_{82}H_{115}N_{13}O_{18}$. (MW = 1571): C, 62.69; H, 7.38; N, 11.59.

b. A mixture of 228 mg. of anhydrous sodium acetate, 229 mg. of the tetra(benzyloxycarbonyl) derivative of antibiotic EM-49 obtained in part a and 5 ml. of acetic anhydride are stirred at 100° for 2 hours. The mixture is cooled, mixed with 40 ml. of water and a little ethyl acetate, then stirred at room temperature for one hour. This mixture is extracted with ethyl acetate and the extract is washed with water, 10% sodium bicarbonate and then water again. The solution is dried ($MgSO_4$) and taken to dryness in vacuo, giving 229 mg. of the tetra(benzyloxycarbonyl)-O-acetyl derivative of antibiotic EM-49.

To prepare an analytical example, a portion of the product is dissolved in methanol, the solution filtered through a short plug of Celite-Darco G60 (1:1) and taken to dryness. The reside is dissolved in methylene chloride and the product precipitated with hexane. The precipitate is isolated by centrifugation, washed several times with hexane and dried in vacuo. Equilibration with atmospheric moisture gives the O-acetyl tetra(benzyloxycarbonyl) derivative of EM-49 containing 2.26% water and melting at 205°–206°C.

Analysis: Found: C, 60.24; H, 7.34; N, 11.42. Adjusted to correspond to the anhydrous material: C, 61.63; H, 7.25; N, 11.68. Calc'd. for $C_{84}H_{117}N_{13}O_{19}$ (MW = 1613): C, 62.55; H, 7.31; N, 11.29.

c. A solution of 122 mg. of the product of part b in 10 ml. of methanol is treated with hydrogen and 10% palladium-carbon (23 mg.) for 20 hours at room temperature. The NMR spectrum shows that not all of the protecting groups are removed. The product is then dissolved in 1 ml. of trifluoroacetic acid. One ml. of a saturated solution of hydrogen bromide in acetic acid is added. After 1 hour, the product is precipitated with ether and then washed with ether. The NMR spectrum now shows that the projecting groups have all been removed. The product, the O-acetyl derivative of antibiotic EM-49, is converted to the hydrchloride, by dissolving in 50 ml. of n-butanol and 50 ml. of water. The pH of the stirred mixture is adjusted to 12 with 5 N sodium hydroxide. The butanol phase is washed twice with 0.01 N sodium hydroxide, once with 84 ml. of 1 N-hydrochloric acid and twice with 0.36 N-hydrochloric acid. The solvent is removed in vacuo and the residue is converted to a powder by dissolving it in methanol, adding ethyl acetate and removing the solvent mixture in vacuo. The hydrochloride of the O-acetyl derivative of antibiotic EM-49 is dried for two hours at 0.02 mm and room temperature, then equilibrated overnight with atmospheric moisture.

The analytical sample has a water content of 9.40%.
Analysis: Found: C, 47.32, H, 7.92; N, 13.26; O (by difference) 21.58; Cl, 9.92; OAc, 3.09. Adjusted to correspond to the anhydrous material: C, 52.53; H, 7.59; N, 14.64; O, 14.59; Cl, 10.95; Acetyl, 3.41.

EXAMPLE 3

A solution of 2.5 g. of antibiotic EM-49 hydrochloride, obtained as in Example 1h, in 25 ml. of trifluoroacetic acid is cooled to 0°, treated with 1.47 ml. of acetyl chloride and stirred at 0° for 1 hour. Addition of ether (125 ml.) gives a precipitate that is washed with ether and dried in vacuo. This product is dissolved in a mixture of 50 ml. of n-butanol and 50 ml. of water and the pH of the stirred mixture is adjusted to 12 with 5 N sodium hydroxide. The butanol phase is washed twice with 0.01 N sodium hydroxide, once with 84 ml. of 1 N-hydrochloric acid and twice with 0.36 N hydrochloric acid. The solvent is removed in vacuo and the residue is converted to a powder by dissolving it in methanol, adding ethyl acetate and removing the solvent mixture in vacuo. The product is dried for two hours at 0.02 mm and room temperature and then equilibrated overnight with atmospheric moisture, giving 2.0 g. of the tetrahydrochloride of the O-acetyl derivative of antibiotic EM-49 containing 7.46% water.

Analysis (on anhydrous material): Found: C, 51.42; H, 8.20; N, 15.16; Cl, 11.29; acetyl, 3.19. Calc'd. for $C_{52}H_{97}N_{13}O_{11}Cl_4$ (MW = 1222): C, 51.10; H, 8.00; N, 14.90; Cl, 11.60; acetyl, 3.52.

Figure 5:
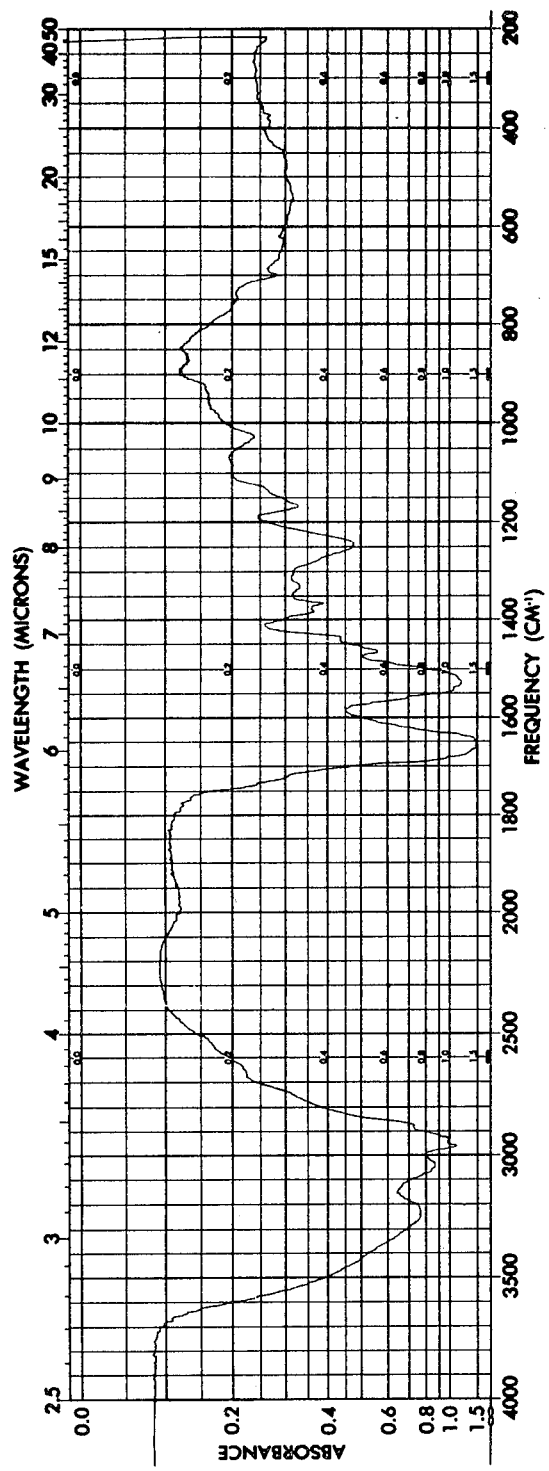
Figure 6:
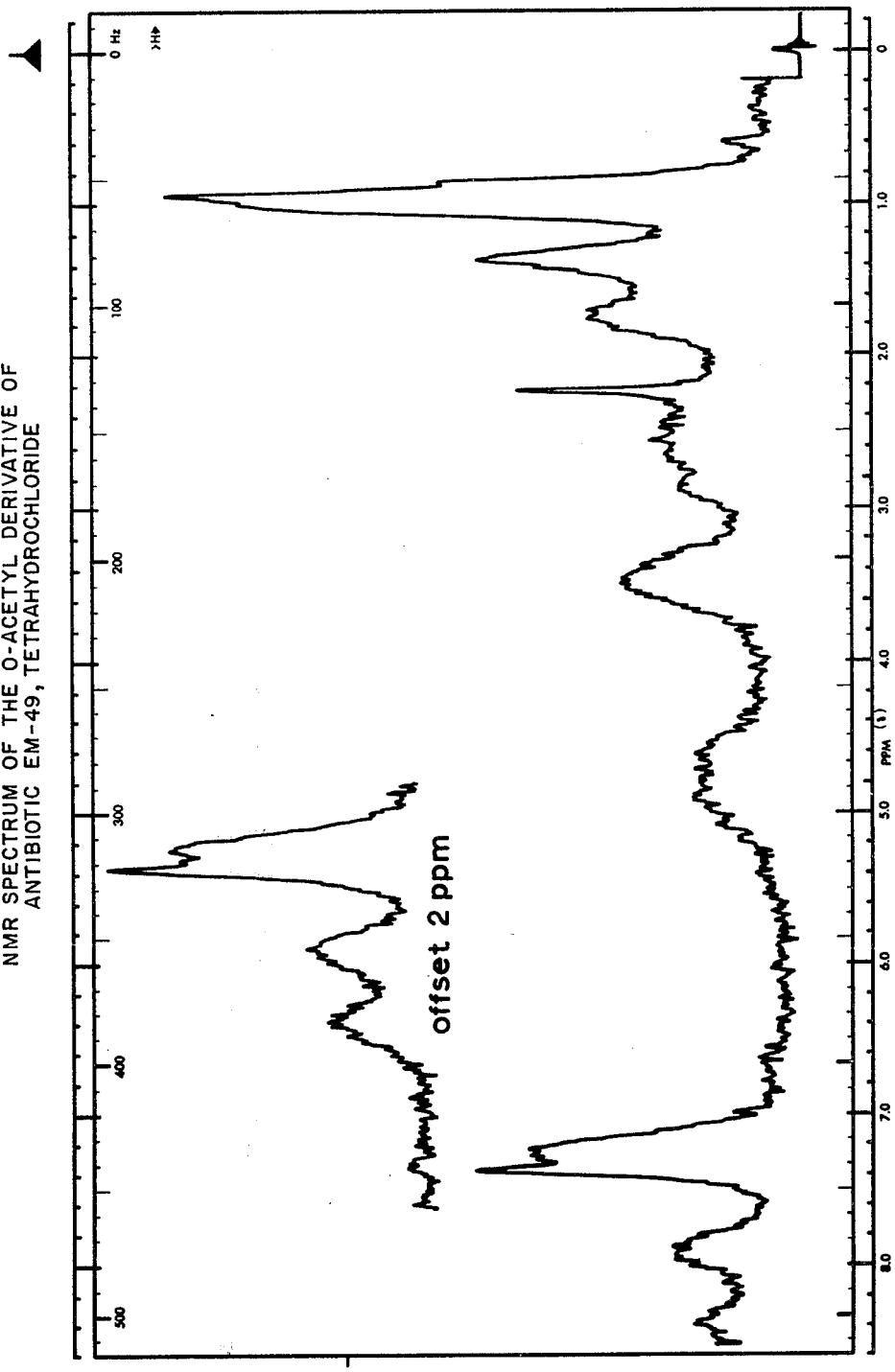
FIG. 6 shows the NMR spectrum of the O-acetyl derivative of antibiotic EM-49, tetrahydrochloride, at 60 MHz in CF$_3$COOH

The O-acetyl group gives a peak at 2.23 ppm. in the NMR spectrum ($CF_3CO_2H$) and a shoulder at 1720 $cm^{-1}$ in the IR spectrum (KBr). The NMR and IR spectra are shown in FIGS. 6 and 5, repectively.

O-acetyl-EM-49 (as the tetrahydrochloride is soluble in water, methanol, dimethylsulfoxide and insoluble in ether, ethyl actate, benzene and chloroform. It melts at 216°–230°C. $R_f$[Gelman ITLC, type SAF (silica acid), n-butanol-propionic acid-water (3:1:1)] 0.66; [Whatman No. 1 paper, n-propanol-n-butanol-water (2:3:4)] 0.51. The O-acetyl derivative is not separated from EM-49 in these systems. The specific rotation is $[\alpha]^{23}$ D - 16.1 (c 1, DMSO).

EXAMPLE 4

2.00 g. (1.59 mmol.) of antibiotic EM-49 hydrochloride is dried in vacuo (0.1 mm, 50°) and then dissolved in 20 ml. of trifluoroacetic acid under argon. The solution is cooled to 0° and 1.66 ml. (16 mmol.) of butyryl chloride are added. The solution is kept at 0° for 1 hour, then the product is precipitated with ether and washed 3 times with ether by centrifugation.

Figure 7:
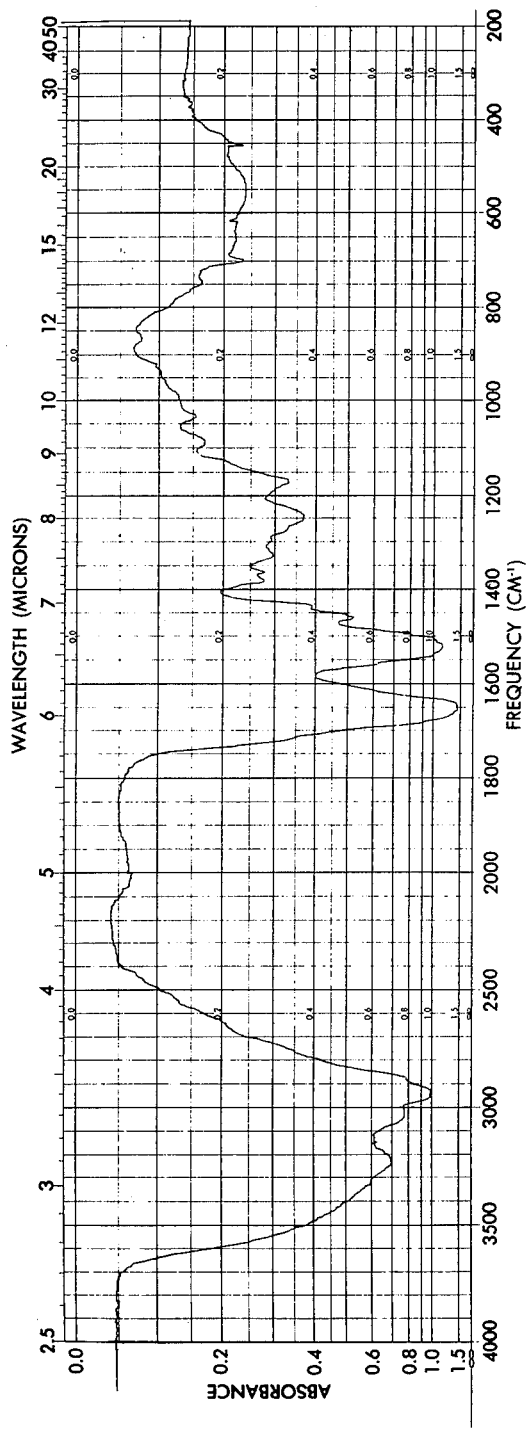
FIG. 7 shows the infrared spectrum of the O-butyryl derivative of antiobiotic EM-49, tetrahydrochloride, in KBr.

The wet cake is dissolved in butanol and water and the resulting mixture concentrated in vacuo to remove residual ether. The mixture is adjusted to pH 8 with saturated sodium bicarbonate solution and a little 1M sodium carbonate solution. The butanol phase is separated, washed with portions of saturated sodium bicarbonate solution until halogen is not detectable in the wash water and then with three portions of 1 N hydrochloric acid. The butanol solution is filtered, concentrated in vacuo, the residue is dissolved in methanol and poured into ether with stirring. The resulting precipitate is separated by centrifugation, washed with ether, dried briefly in vacuo, powdered, and then dried overnight in vacuo (50°, 0.02 mm), giving 1.76 g. (88% yield) of O-butyryl-EM-49 tetrahydrochloride. The product is equilibrated with atompsheric moisture, giving 1.87 g. (5.97% water), m.p. 216° $R_f$ 0.57 (silica gel, PrOH-conc. NH$_4$OH, 7:3). The infrared spectrum is shown in FIG. 7.

Analysis calc'd. for $C_{54}H_{101}N_{13}O_{11}Cl_4$ (M.W. 1250.30): C, 51.94; H, 8.16; N, 14.53; Cl$^-$, 11.32. Found: C, 49.32; H, 7.91; N, 13.54; Cl$^-$, 10.50. Adjusted for water (% found ÷ 0.9403): C, 52.45, N, 14.40, Cl$^-$, 11.17.

EXAMPLE 5

Figure 8:
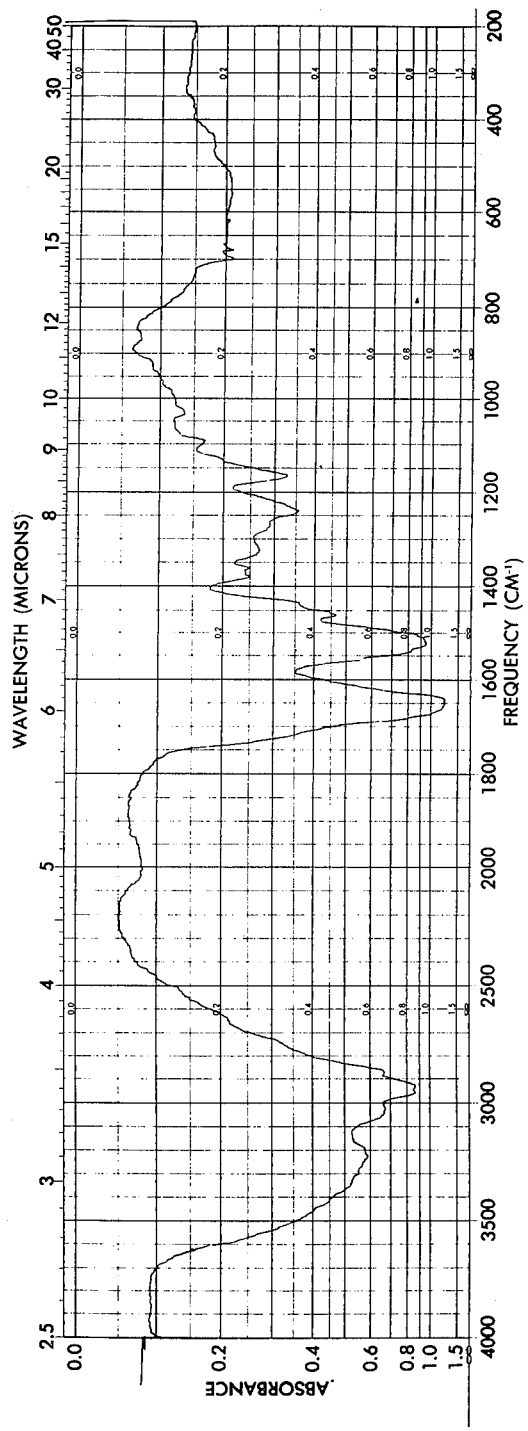
FIG. 8 shows the infrared spectrum of the O-hexanoyl derivative of antibiotic EM-49, tetrahydrochloride, in KBr.

The O-hexanoyl derivative of antibiotic EM-49 hydrochloride is prepared from 2 g. of antibiotic EM-49 hydrochloride and hexanoyl chloride (2.21 ml., 16 mmol.) by the procedure of Example 4. However, the reaction is carried out at room temperature instead of 0°. The yield of dry O-hexanoyl-EM-49 hydrochloride is 1.78 g. (87%). Equilibration with atmospheric moisture gives 1.85 g. (4.06% H$_2$O) of product, m.p. 215° $R_f$ 0.49 (silica gel, PrOH-conc. NH$_4$OH, 7:3). The infrared spectrum is shown in FIG. 8.

Analysis calc'd. for $C_{56}H_{105}N_{13}O_{11}Cl_4$ (M.W. 1278.35): C, 52.68; H, 8.30; N, 14.21; Cl$^-$, 11.07; Found: C, 50.71; H, 7.99; N, 13.32; Cl$^-$, 10.52; Adjusted for H$_2$O (%found ÷ 0.9594): C,52.86 N, 13.88; Cl$^-$, 10.97.

EXAMPLE 6

54 mg. of O-hexanoyl-EM-49 hydrochloride is dissolved in a mixture of n-butanol and water. The pH of the mixture is adjusted to 10.0 with 0.1 N sodium hydroxide. The upper phase is separated, washed twice with 0.01 N sodium hydroxide and then with water until the aqueous wash is neutral. The butanol solution is taken to dryness in vacuo and the residue is dissolved in methanol. Benzene and heptane are added and the mixture is concentrated in vacuo to remove the methanol. The resulting precipitate is separated, washed with heptane and dried in vacuo, giving 43.7 mg. (98% yield) of the O-hexanoyl derivative of antibiotic EM-49, as an amorphous solid.

Figure 9:
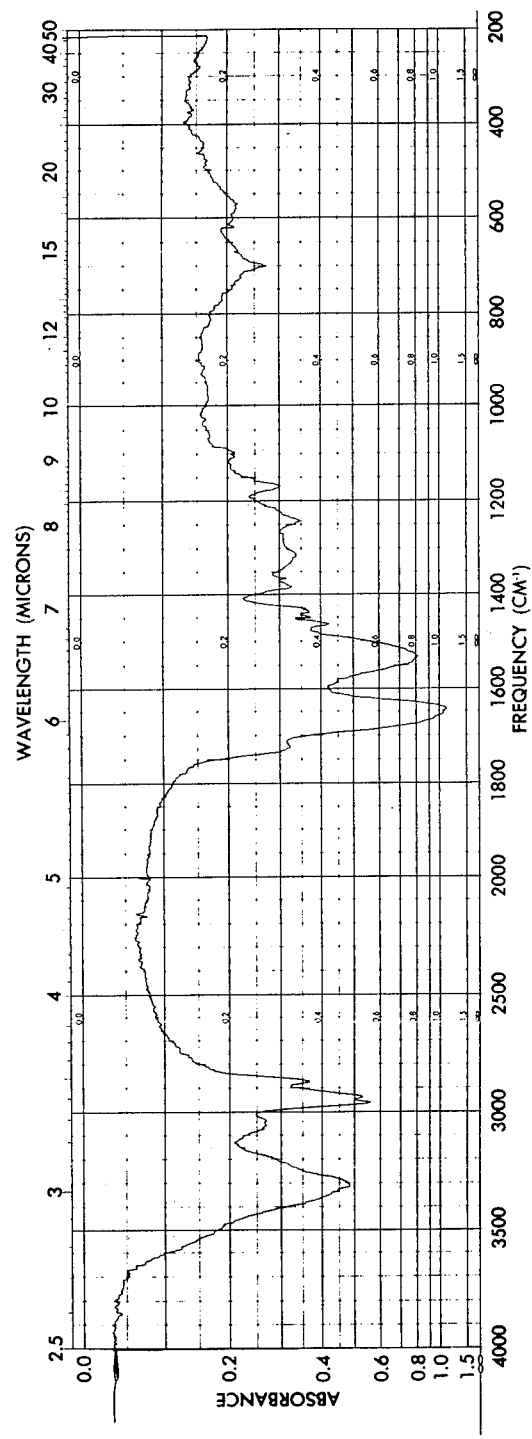
FIG. 9 shows the infrared spectrum of the O-hexanoyl derivative of antibiotic EM-49 in KBr.

A portion of this material is powdered and dried at 0.05 mm and 50° for 17 hours and then equilibrated with atmospheric moisture, giving material containing 5.77% water, m.p. 213°–218° (dec.). The infrared spectrum is shown in FIG. 9.

Analysis: Calc'd. for $C_{56}H_{101}N_{13}O_{11}$ (M.W. 1132.5) C, 59.39; H, 8.99; N, 16.08. Found: C, 56.38; H, 8.00; N, 14.85. Adjusted for water (% found ÷ 0.9423): C, 59.83; N, 15.76. Neutral equivalent (HClO$_4$); Calc'd. = 300.5; found 315.

EXAMPLE 7

0.50 g. of antibiotic EM-49 hydrochloride is dried in vacuo (50°, 0.1 mm, 0.5 hr) and then dissolved in 5 ml. of trifluoroacetic acid under argon. 0.55 ml. (4.0 mmol.) of hexanoyl chloride are added and the solution is left at room temperature for 1 hour. The product is precipitated by the addition of ether, separated by centrifugation and washed three times with ether.

The wet cake is dissolved in a mixture of n-butanol and water and the residual ether is removed in vacuo. The mixture is adjusted to PH 8 with saturated aqueous sodium bicarbonate and a little 1 M sodium carbonate solution. The butanol phase is separated, washed three times with saturated sodium bicarbonate solution and then water until the wash is neutral.

Figure 10:
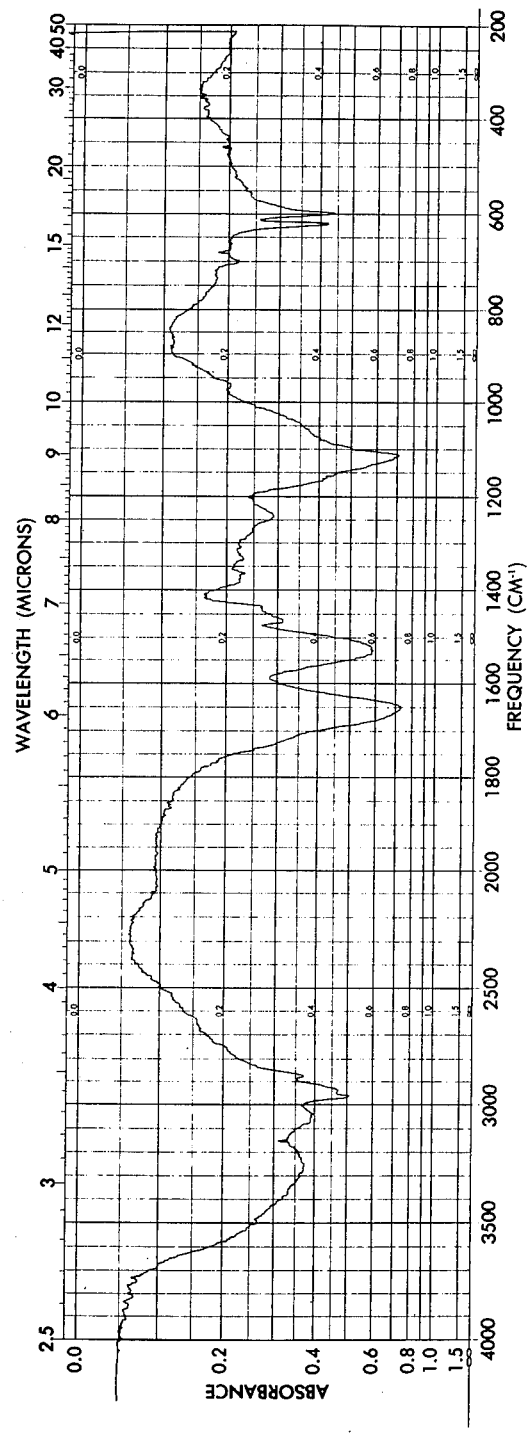
FIG. 10 shows the infrared spectrum of the O-hexanoyl derivative of antibiotic EM-49, sulfate salt, in KBr.

The butanol solution is filtered, mixed with a little water and adjusted to pH 3.8 with 1N sulfuric acid. The mixture is taken to dryness in vacuo and the residue is dissolved in methanol (warm). The product is precipitated by the addition of ether, separated by centrifugation, washed with ether, and dried in vacuo, giving 0.51 g. (96%) of O-hexanoyl EM-49 sulfate salt. A portion of this material is powdered, dried in vacuo (0.05 mm., 50°, 17 hr.) and equilibrated with atmospheric moisture (48 hr.), giving the product as an amorphous solid containing 10.63% water, m.p. 235° (dec.). The infrared spectrum is shown in FIG. 10.

Analysis calc'd. for $C_{56}H_{105}N_{13}O_{19}S_2$ (M.W. 1328.67); C, 50.62; H, 7.97; N,13.71; SO$_4^=$, 14.46%. Found: C, 44.85; H, 7.46; N, 12.05; SO$_4^=$, 12.60 Adjusted for water (% found ÷ 0.8937): C, 50.18; N, 13.48; SO$_4^=$, 14.10 Neutral equivalent: Calc'd. = 372; found 351.

EXAMPLE 8

0.50 g. of antibiotic EM-49 hydrochloride is dried in vacuo (50°, 0.1 mm, 0.5 hr) and then dissolved in 5 ml. of trifluoroacetic acid under argon. Hexanoyl chloride, 0.55 ml. (4.0 mmol), is added and the solution is left at room temperature for 1 hour. The product is precipitated by the addition of ether, separated by centrifugation and washed three times with ether.

The wet cake is dissolved in a mixture of n-butanol and water and the residual ether removed in vacuo. The mixture is adjusted to pH 8 with saturated aqueous sodium bicarbonate and a little 1 M sodium carbonate solution. The butanol is separated, washed three times with saturated sodium bicarbonate solution and then water until the wash is neutral.

Figure 11:
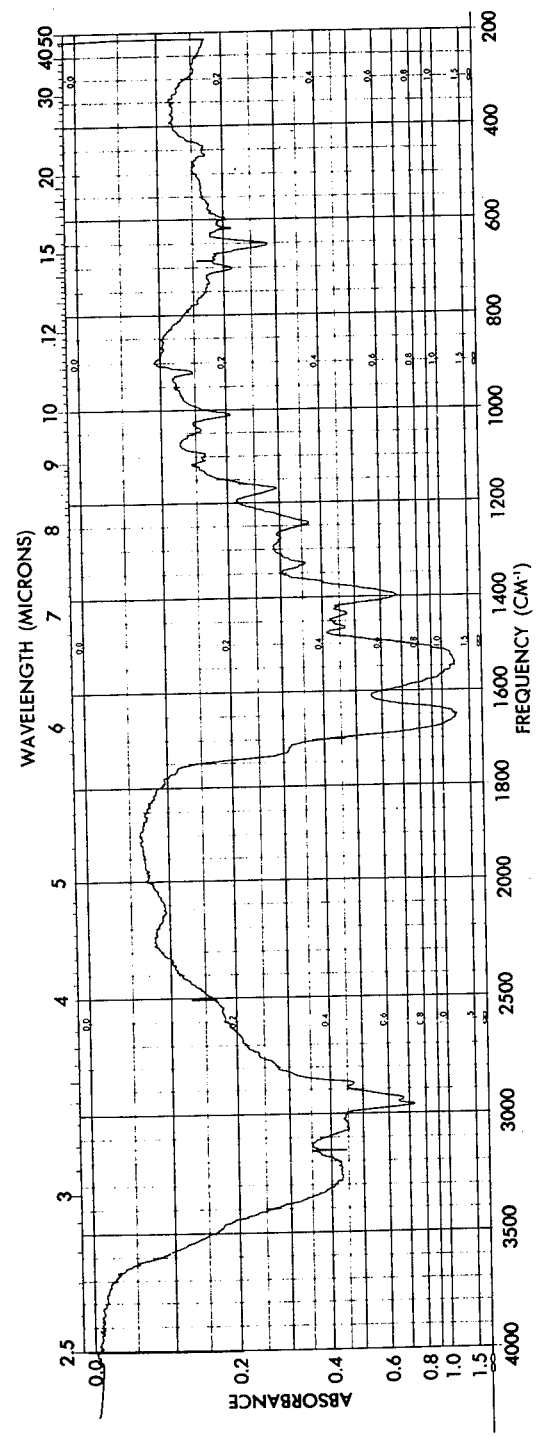
FIG. 11 shows the infrared spectrum of the O-hexanoyl derivative of antibiotic EM-49, acetate salt, in KBr.

The butanol solution is filtered, mixed with 1 ml. of glacial acetic acid and taken to dryness in vacuo. The residue is dissolved in methanol and the product precipitated by the addition of ether, separated by centrifugation, washed with ether and dried in vacuo, giving 0.47 g. of solid (86% yield) O-hexanoyl EM-49 acetate salt. A portion is powered, dried (0.05 mm, 50°, 17 hr), and equilibrated with atmospheric moisture, giving the product as an amorphous solid containing 10.78% water, m.p. 197° (dec.). The infrared spectrum is shown in FIG. 11.

Analysis: Calc'd. for $C_{64}H_{117}N_{13}O_{19}$ (M.W. 1372.72); C, 56.00; H, 8.59; N, 13.27; HOAc, 17.50. Found: C, 51.35; H, 7.92; N, 12.04; HOAc, 14.79 Adjusted for water (% found ÷ 0.8922): C, 57.55; N, 13.49; HOAc, 16.58

EXAMPLE 9

Figure 12:
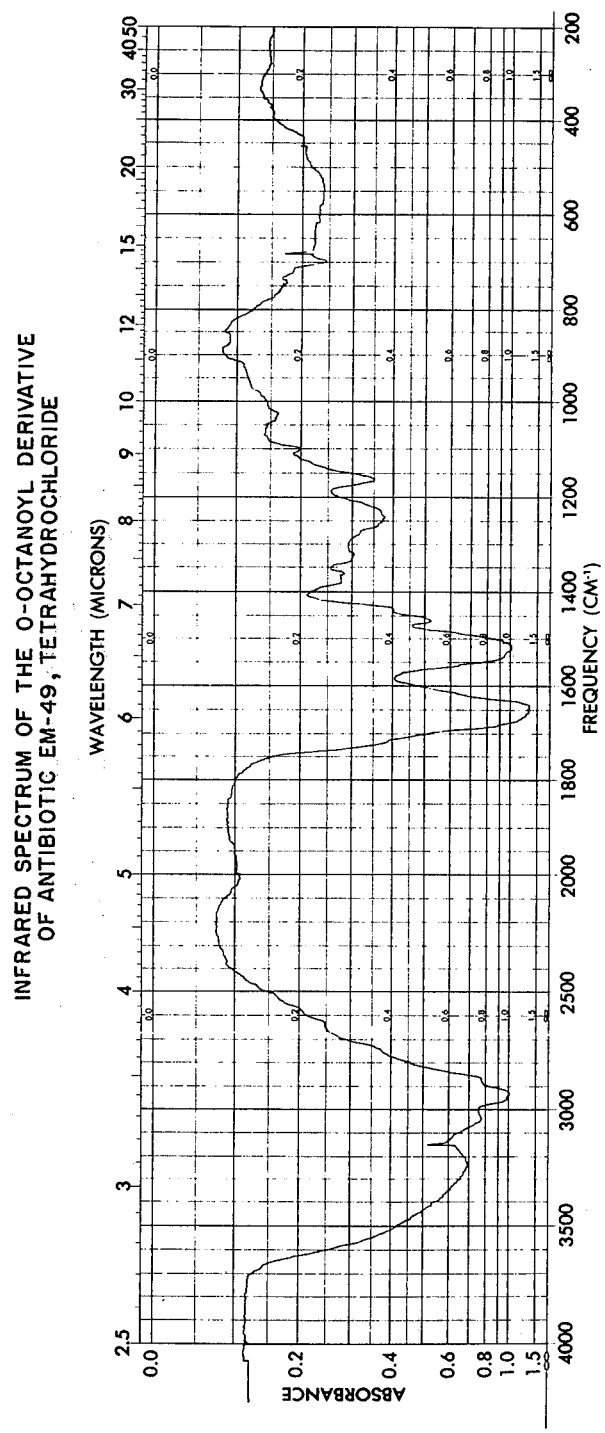
FIG. 12 shows the infrared spectrum of the O-octanoyl derivative of antibiotic EM-49, tetrahydrochloride, in KBr.

The O-octanoyl derivative of EM-49 hydrochloride is prepared from antibiotic EM-49 hydrochloride, (2g., 1.59 mmol.) and octanoyl chloride (2.73 ml., 16 mmol.) using the procedure of Example 4. The reaction, however, is carried out at room temperature instead of 0°. The yield of dry O-octanoyl EM-49 hydrochloride is 1.80 g. (87%). Equilibration with atmospheric moisture gives 1.88 g. (4.01% water) of product, m.p. 215°, $R_f$ 0.49 (silica gel eluting with propanol-conc. NH$_4$OH, 7:3). The infrared spectrum is shown in FIG. 12.

Analysis: calc'd. for $C_{58}H_{109}N_{13}O_{11}Cl_4$ (M.W. 1306.41): C, 53.39; H, 8.43; N, 13.91; Cl$^-$, 10.83; Found: C, 51.97; H, 8.37; N, 12.96; Cl$^-$, 10.12; Adjusted for water (% found ÷ 0.9599): C, 54.14; N, 13.50; Cl⁻, 10.54.

What is claimed is:

1. The O-acetyl derivative of antibiotic EM-49 and acid salts thereof, the hydrochloride having the infrared absorption spectrum as in FIG. 5, the NMR spectrum as in FIG. 6, the approximate elemental analysis of anhydrous material: C, 51.10; H, 8.00; N, 14.90; Cl, 11.60; the approximate empirical formula $C_{52}H_{97}N_{13}O_{11}Cl_4$ and an approximate molecular weight of 1222.

2. The hydrochloride of the product of claim 1.

Figure 2:
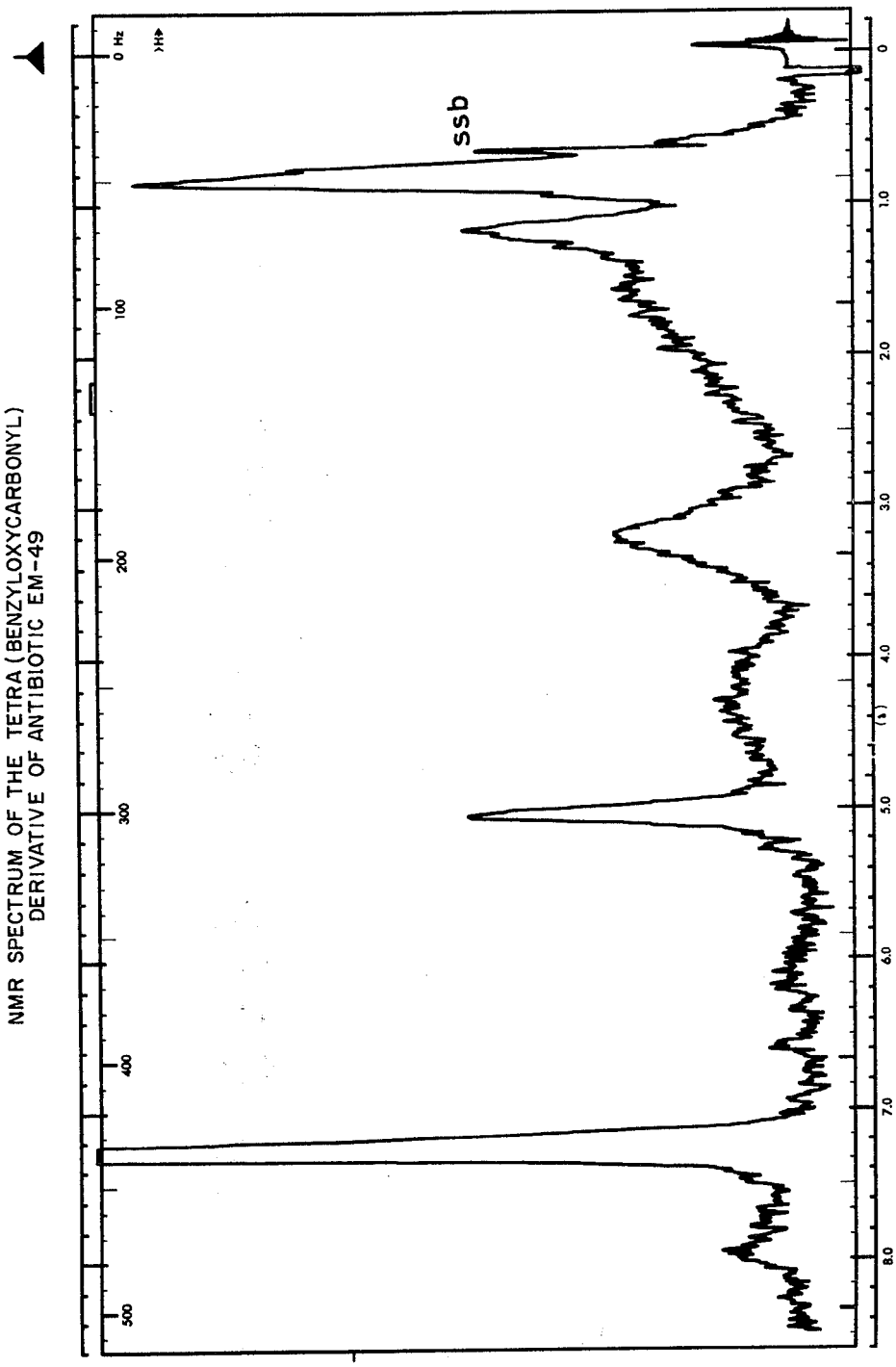
FIG. 2 shows the NMR spectrum of the tetra(benzyloxycarbonyl) derivative of antibiotic EM-49, at 60 MHz in CDCl$_3$.

3. The tetra(benzyloxycarbonyl) derivative of antibiotic EM-49 having the infrared absorption as in FIG. 1, the NMR spectrum as in FIG. 2, the approximate elemental analysis of anhydrous material: C, 61.27; H, 6.69; N, 11.37; the approximate empirical formula $C_{82}H_{115}N_{13}O_{18}$ and an approximate molecular weight of 1571.

Figure 3:
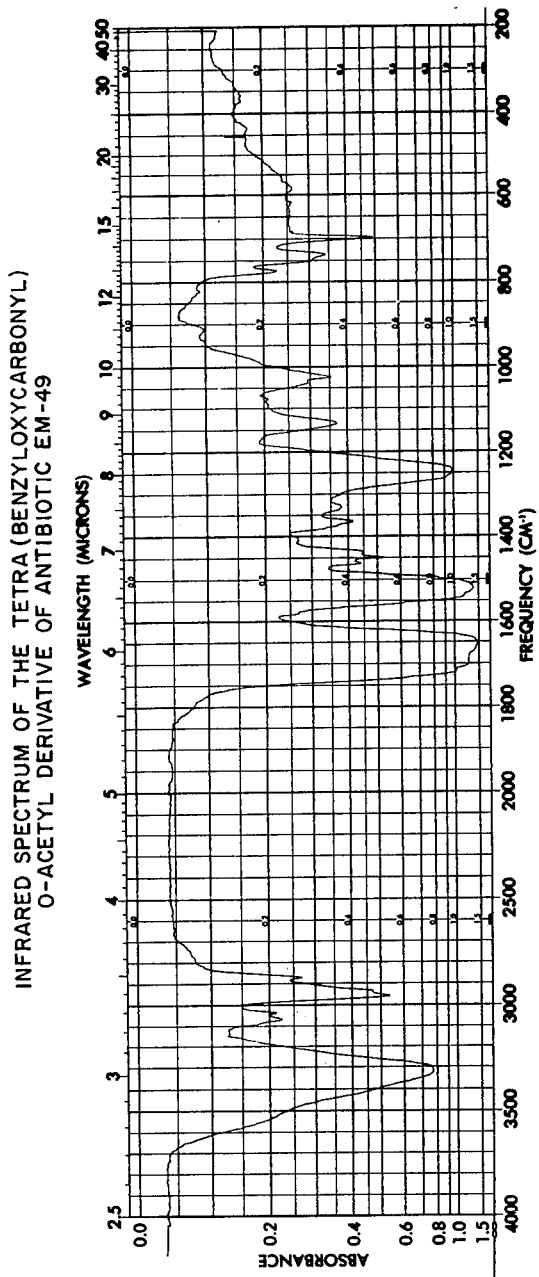
FIG. 3 shows the infrared spectrum of the tetra(benzyloxycarbonyl)-O-acetyl derivative of antibiotic EM-49 in KBr.
Figure 4:
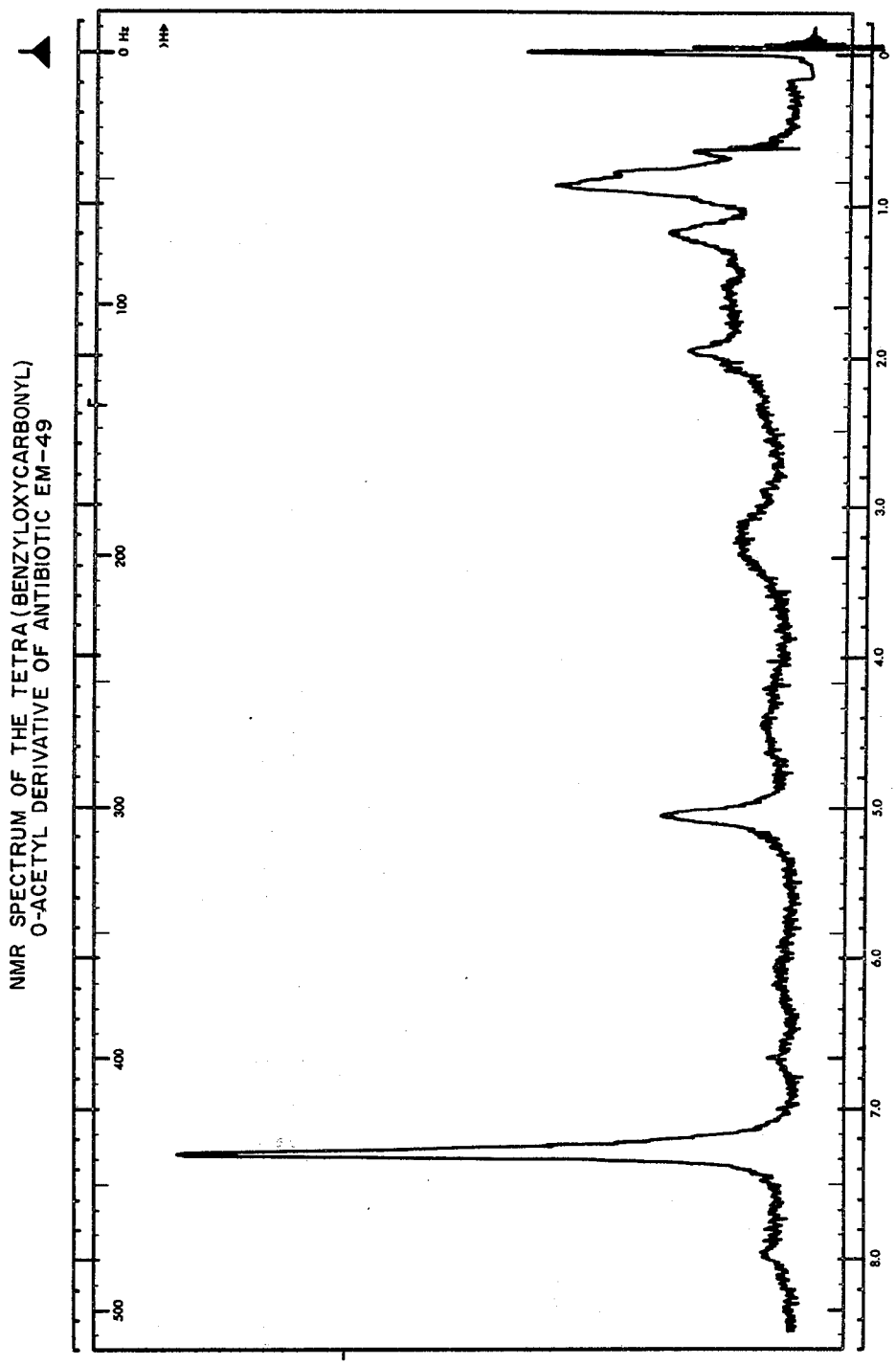
FIG. 4 shows the NMR spectrum of the tetra(benzyloxycarbonyl)-O-acetyl derivative of antibiotic EM-49, at 60 MHz in CDCl$_3$.

4. The tetra(benzyloxycarbonyl)-O-acetyl derivative of antibiotic EM-49, having the infrared absorption spectrum as in FIG. 3, the NMR spectrum as in FIG. 4, the approximate elemental analysis of anhydrous material: C, 61.63; H, 7.25; N, 11.68; the approximate empirical formula $C_{84}H_{117}N_{13}O_{19}$ and an approximate molecular weight of 1613, and acid salts thereof.

5. The O-butyryl derivative of antibiotic EM-49 and acid salts thereof, the hydrochloride having the infrared absorption spectrum as in FIG. 7, the approximate elemental analysis of anhydrous material, as the hydrochloride: C, 52.45; N, 14.40; Cl⁻, 11.17; the approximate empirical formula $C_{54}H_{101}N_{13}O_{11}Cl_4$ and an approximate molecular weight of 1250.

6. The O-hexanoyl derivative of antibiotic EM-49, and acid salts thereof, having the infrared absorption spectrum as in FIG. 9, the approximate elemental analysis of anhydrous material: C, 59.83; N, 15.76; the approximate empirical formula $C_{56}H_{101}N_{13}O_{11}$ and an approximate molecular weight of 1132.

7. The O-octanoyl derivative of antibiotic EM-49, and acid salts thereof, the hydrochloride having the infrared spectrum as in FIG. 12, the approximate elemental analysis: C, 51.97; H, 8.37; N, 12.96; Cl⁻, 10.12; the approximate empirical formula $C_{58}H_{109}N_{13}O_{11}Cl_4$ and an approximate molecular weight of 1306.

8. A compound of the formula

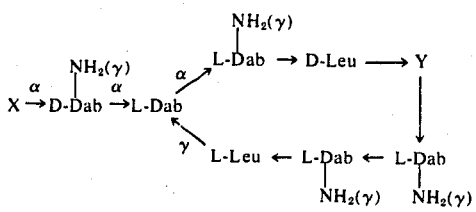

wherein Dab is 2,4-diaminobutyric acid, Y is L-leucine or L-phenylalanine; X is

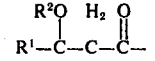

$R^1$ is $C_7H_{15}$ or $C_8H_{17}$; and $R^2$ is lower alkanoyl, and acid salts thereof.

9. A compound as in claim 8 wherein Y is L-leucine.

10. A compound as in claim 8 wherein Y is L-phenylalanine.

11. A compound as in claim 8 wherein $R^2$ is acetyl.

12. A compound as in claim 8 wherein $R^2$ is butyryl.

13. A compound as in claim 8 wherein $R^2$ is hexanoyl.

14. A compound as in claim 8 wherein $R^2$ is octanoyl.

15. Acid addition salt of a compound as in claim 13.

16. Hydrochloride of a compound as in claim 13.

17. A compound as in claim 9 wherein $R^1$ is $C_7H_{15}$ and $R^2$ is acetyl.

18. A compound as in claim 9 wherein $R^1$ is $C_8H_{17}$ and $R^2$ is acetyl.

19. A compound as in claim 9 wherein R is $C_7H_{15}$ and $R^2$ is butyryl.

20. A compound as in claim 9 wherein $R^1$ is $C_8H_{17}$ and $R^2$ is butyryl.

21. A compound as in claim 9 wherein $R^1$ is $C_7H_{15}$ and $R^2$ is hexanoyl.

22. A compound as in claim 9 wherein $R^1$ $C_8H_{17}$ and $R^2$ is hexanoyl.

23. A compound as in claim 9 wherein $R^1$ is $C_7H_{15}$ and $R^2$ is octanoyl.

24. A compound as in claim 9 wherein $R^1$ is $C_8H_{17}$ and $R^2$ is octanoyl.

25. A compound as in claim 10 wherein $R^1$ is $C_7H_{15}$ and $R^2$ is acetyl.

26. A compound as in claim 10 wherein $R^1$ is $C_8H_{17}$ and $R^2$ is acetyl.

27. A compound as in claim 10 wherein $R^1$ is $C_7H_{15}$ and $R^2$ is butyryl.

28. A compound as in claim 10 wherein $R^1$ is $C_8H_{17}$ and $R^2$ is butyryl.

29. A compound as in claim 10 wherein $R^1$ is $C_7H_{15}$ and $R^2$ is hexanoyl.

30. A compound as in claim 10 wherein $R^1$ is $C_8H_{17}$ and $R^2$ is hexanoyl.

31. A compound as in claim 10 wherein $R^1$ is $C_7H_{15}$ and $R^2$ is octanoyl.

32. A compound as in claim 10 wherein $R^1$ is $C_8H_{17}$ and $R^2$ is octanoyl.

33. A compound as in claim 10 wherein X is 2-hexanoyloxy-8-methyldecanoyl.

* * * * *